US006518033B1

(12) United States Patent
Gromeier et al.

(10) Patent No.: US 6,518,033 B1
(45) Date of Patent: Feb. 11, 2003

(54) METHOD OF DETECTING THE PRESENCE OF CD155 FOR DIAGNOSIS OF CANCER AND TO DETERMINE TREATMENT

(75) Inventors: Matthias Gromeier, Durham, NC (US); Eckard Wimmer, East Setauket, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/655,744

(22) Filed: Sep. 6, 2000

Related U.S. Application Data

(63) Continuation-in-part of application No. 09/262,614, filed on Mar. 4, 1999, now abandoned, which is a continuation-in-part of application No. 09/129,686, filed on Aug. 5, 1998, now Pat. No. 6,264,940.

(51) Int. Cl.[7] ............................................. G01N 33/574
(52) U.S. Cl. .................... 435/7.23; 435/7.92; 435/7.95; 435/40.52; 436/518; 436/527
(58) Field of Search ............................. 435/7.92, 7.95, 435/40.52, 7.23; 436/518, 527

(56) References Cited

U.S. PATENT DOCUMENTS

| 5,631,407 A | 5/1997 | Racaniello et al. | ............ 800/2 |
| 5,753,521 A | 5/1998 | Racaniello et al. | ........ 435/69.1 |

OTHER PUBLICATIONS

Koike et al., *Proc. Natl. Acad. Sci. U.S.A.* (1991) 88:951–955.
Mendelsohn C. et al., *Proc. Natl. Acad. Sci.* USA (1986) 83:7845–7849.
Nobis, P. et al. *J. Gen. Virol.*, (1985) 66:2563–2569.
Ren, R. et al., *Cell* (1990) 63:353–362.
Sasaki, H. et al. *Cancer*, (1998) 82:1921–1931.
Tsuzuki, T. et al. *J. Clin. Pathol.*, (1998) 51:13–17.
Walsh et al., *Annul Rev.Cell Dev. Biol.* (1997) 13:425–456.
Wimmer et al., In: *Cellular Receptors for Animal Viruses* (1993) 7:101–127, Cold Spring Laboratory Press: Planview. NY.
Bodian D., *Science* (1955) 12:105–108.
Bernhardt et al., *Virology* (1994) 203: 344–356.
Chadeneau et al., *Int. J. Cancer* (1994) 68:817–821.
Colamarino et al., *Annul Rev. Neurosci.* (1995) 18:497–529.
Figarella–Branger et al., *Cancer Res.* (1990) 50:6364–6370.
Gingras, M.–C. et al. *J. Neuroimmunol.*, (1995) 57:143–153.
Gromeier et al., *Proc. Natl. Acad. Sci. U.S.A.* (1996) 93:2370–2375.
Gromeier, M. et al., *J. Virol.*, (1999) 73:5056–60.
Izumoto, S. et al., *Cancer Res.*, (1996) 56:1440–1444.
Koike et al., *EMBO J.* (1990) 9:3217–3229.

*Primary Examiner*—Donna C. Wortman
(74) *Attorney, Agent, or Firm*—Scully, Scott, Murphy & Presser

(57) ABSTRACT

The present invention relates to a method of diagnosing, classifying and grading of tumor growths and to determine whether the use of chimeric polioviruses is a proper course for the treatment of the tumors. More particularly, the method is directed to the use of antibodies to a poliovirus receptor (PVR), CD155, to detect the presence of CD155 on tumor cells in various organs, such as: breast, colon, bronchial passage, epithelial lining of the gastrointestinal, upper respiratory and genito-urinary tracts, liver, prostate and the brain.

13 Claims, 2 Drawing Sheets

Combined Immunoprecipitation/Western blot analysis of CD155 expression in normal brain tissues and brain tumor tissues

1. mouse brain (200mg)
2. human spinal cord (150mg)
3. glioma (40mg)
4. human brain (400mg)

METHOD OF DETECTING THE PRESENCE OF CD155 FOR DIAGNOSIS OF CANCER AND TO DETERMINE TREATMENT

CROSS REFERENCE TO RELATED APPLICATION

The present application is a continuation-in-part application of application Ser. No. 09/262,614, filed Mar. 4, 1999, abandoned, which is in turn a continuation-in-part application of application Ser. No. 09/129,686 filed Aug. 5, 1998, now U.S. Pat. No. 6,264,940.

The invention was made with Government support under No. AI32100-07 and AI39485 awarded by the National Institutes of Health. The government has certain rights in the invention.

The present invention relates to a method of diagnosing, classifying and grading of tumor growths and to determine whether the use of chimeric polioviruses is a proper course for the treatment of the tumors. More particularly, the method is directed to the use of antibodies to a poliovirus receptor (PVR), CD155, to detect the presence of CD155 on tumor cells in various organs, such as: breast, colon, bronchial passage, epithelial lining of the gastrointestinal, upper respiratory and genito-urinary tracts, liver, prostate and the brain.

BACKGROUND OF THE INVENTION

It has been found by the inventors that malignant tumors can be successfully treated with chimeric polioviruses wherein the internal ribosomal entry site (IRES) is replaced with the IRES of another picornavirus. This finding is the subject of U.S. patent application Ser. No. 09/129,686, incorporated herein by reference.

Poliovirus is a small iscosahedral RNA virus belonging to the picornavirus family. It is best known as the etiologic agent of poliomyelitis, the visible clinical sign of which is flaccid paralysis. The virus when ingested, infects and replicates in the gut, leading to viremia. In a small portion of infected individuals, the virus invades the central nervous system through the circulation. It is the lytic replication in motor neurons of the brain stem and spinal cord that causes destruction of these cells and the characteristic flaccid paralysis of poliomyelitis. Bodian D., *Science* (1955) 12:105–108. It is known that poliovirus invades only a limited number of specific cells in the body, an unknown population of cells lining the gastrointestinal tract and spinal cord anterior horn as well as medullary motor neurons. It is the unusual restricted cell tropism of poliovirus that leads to unique pathognomonic features, characterized by motor neuron loss in the spinal cord and the medulla, giving rise to the hallmark clinical sign of poliomyelitis, flaccid paralysis, Bodian, D., supra. The restricted tropism of poliovirus is poorly understood. In addition to the restricted cell and tissue tropism, poliovirus only infects primates and primate cell cultures. Other mammalian species remain unaffected. Ren, R. et al., *Cell* (1990) 63:353–362.

The isolation of poliovirus in 1908 led to intensive research efforts to understand the mechanisms of infection. The earlier work required the use of monkeys and chimpanzees as animal models. Such animals with longer life cycles are very costly and difficult to use in research. The discovery of the human poliovirus receptor (PVR), the cellular docking molecule for poliovirus, led to the development of a transgenic mouse expressing the human poliovirus receptor as a new animal model for poliomyelitis. Mice transgenic for PVR, when infected with poliovirus, develop a neurological syndrome histopathologically and clinically identical to primate poliomyelitis. Koike et al., *Proc. Natl. Acad. Sci. U.S.A.* (1991) 88:951–955. The observation of poliomyelitis in polio-infected transgenic animals suggests that CD155 alone is responsible for directing poliovirus towards spinal cord anterior horn motor neurons mediating their infection and subsequent lytic destruction. Gromeier et al., *Proc. Natl. Acad. Sci. U.S.A.* (1996) 93:2370–2375. The poliovirus receptor, previously referred to as PVR, has now been classified as CD155. Mendelsohn C. et al., *Cell* (1989) 56:855–865 and U.S. Pat. Nos. 5,631,407 and 5,753,521.

Up to the present, CD155 has not been associated with malignant tumors. Polypeptide CD155 is a cell-surface protein belonging to the immunoglobulin superfamily. Its gene is the founding member of a new family of primate and rodent genes that encode polypeptides with a common structural arrangement of three extracellular (V-C2-C2) domains. CD155 is expressed in four isoforms: hPVRα and hPVRδ are membrane-bound variants that differ only in the sequence of the cell-internal C-terminal domain, while hPVRβ and hPVRγ are secreted isoforms lacking the transmembrane domain. Koike et al., *EMBO J.* (1990) 9: 3217–3229; Wimmer et al., In: *Cellular Receptors for Animal Viruses* (1993) Cold Spring Laboratory Press: Plainview. N.Y. hPVRα and hPVRδ are type Ia single-pass transmembrane glycoproteins with apparent $M_r$ of >80 kDa, whereas the core polypeptides are 42.5 and 40 kDa, respectively. Binding of poliovirus occurs at the V-domain of the polypeptide. Bernhardt et al., *Virology* (1994) 203: 344–356.

First indications for an association between CD155 and cancer are based on assays making use of polioviruses to infect and destroy tumor cells derived from human malignancies. In co-pending U.S. application Ser. No. 09/129,686, the effectiveness of recombinant chimeric polioviruses for the treatment of various forms of cancer was desribed. Human tumor cells obtained from explant surgical material were susceptible to poliovirus whereas their non-malignant progenitors are known to resist poliovirus infection. It was suspected that the acquisition of susceptibility to poliovirus is based on the overexpression of the cellular receptor for poliovirus on cells upon malignant transformation. A precedent for this assumption is provided by a homolog of CD155 in rodents, the murine Tage4 molecule. Tage4 was isolated from rodent colon- and mammary carcinomas, where it occurs in abundance. Chadeneau et al., *Int. J. Cancer* (1994) 68:817–821. In contrast, Tage4 could hardly be detected in normal rodent colon- or mammary duct epithelium. Chadeneau et al., supra.

The link of CD155 with cancer is further evident from studies of the expression of CD155 during embryonic development. Like many of its fellow members of the immunoglobulin superfamily, CD155 appears to be expressed during embryonic development. Frequently, immunoglobulin superfamily molecules that are expressed in a developmental manner have been associated with malignancy. It has been determined that CD155 may be expressed in a group of highly specialized structures within the embryonic central nervous system, e.g., floor plate, notochord, and optic nerve. These studies not only provided evidence for the distribution of CD155 in the developing nervous system but also pointed towards a physiological function of CD155 that may encompass a role during morphogenesis of the central nervous system. Molecules related to CD155 in structure or sequence are known to be expressed with an overlapping distribution during central nervous system ontogeny. Walsh et al., *Annul Rev. Cell Dev. Biol.* (1997) 13:425–456; Colamarino et al., *Annul Rev. Neurosci.* (1995) 18:497–529.

Molecules of the immunoglobulin superfamily, for example Tage4 (see above), are increasingly recognized for their association with cancer. Sasaki et al., *Cancer* (1998) 82:1921–1931; Gingras et al., *J. Neuroimmunol.* (1995) 57:143–153; Figarella-Branger et al., *Cancer Res.* (1990) 50:6364–6370. It is believed that molecules belonging to the immunoglobulin superfamily with a function involving the mediation of cell adhesion and axonal guidance are frequently overexpressed in malignant tumors. Their physiological functions may be of relevance for the biology of tumors. Aberrant properties of tumor cells, for example invasiveness, migration and metastatic spread may correlate to the expression of immunoglobulin superfamily molecules with a function in cell adhesion. Izumoto et al., *Cancer Res.* (1996) 56:1440–1444. Corroborating the findings with other cell adhesion molecules of the immunoglobulin superfamily with a role in embryonic development of the CNS we provided extensive evidence that CD155, indeed, is abundant in a variety of human malignancies (see below).

Antibodies to CD155

Monoclonal antibodies which recognize CD155 have been developed. In particular, a murine monoclonal antibody was developed by immunizing mice with plasma membrane preparations of HeLa cells. The monoclonal antibody D171 was selected for its ability to protect HeLa cells against the cytopathic effect of poliovirus. It was found that the antibody or its Fab fragments bound to cell lines of human or primate origin and such binding can be blocked after pre-incubation with poliovirus. Nobis, P. et al. *J. Gen. Virol.*, (1985) 66:2563–2569. HeLa cell membrane preparations were used in order to raise monoclonal antibodies against the receptor for poliovirus because they were the most commonly available cell line to propagate poliovirus in tissue culture. HeLa cells are derived from a human cervix carcinoma. Carcinoma cell lines that had been adapted to tissue culture through many hundred passages are commonly used to propagate poliovirus. The ability of these cell lines to efficiently replicate poliovirus implies that they must express CD155. However, the relation of CD155 with cancer was not obvious. Carcinoma cell lines (such as HeLa cells) routinely used for tissue culture purposes may have little in common with the tumor cells from which they were originally derived. An association of CD155 with human malignancies was first recognized by the inventors. This association only became evident after direct immunological probing for CD155 in human surgical tumor explants. The approach employed assured that expression levels of CD155 measured actually correspond to those in tumors found in cancer patients, rather than in tissue culture cell lines established decades ago that have been passaged innumerable times, e.g., HeLa cells.

Recombinant Polioviruses

Chimeric polioviruses carrying heterologus IRES elements, which have lost their inherent neuropathogenic potential have been described. Gromeier, M. et al., supra. Mice transgenic for PVR, when infected with poliovirus, develop a neurological syndrome histopathologically and clinically identical to primate poliomyelitis. Koike et al., *Proc. Natl. Acad. Sci. U.S.A.* (1991) 88:951–955. The observation of poliomyelitis in polio-infected transgenic animals suggests that CD55 alone is responsible for directing poliovirus towards spinal cord anterior horn motor neurons mediating their infection and subsequent lytic destruction. Gromeier et al., *Proc. Natl. Acad. Sci. U.S.A.* (1996) 93:2370–2375. Gromeier et al., *J. Virol.* (1999) 73:5056–5060 incorporated herein by reference. It was found that the substitution of the cognate IRES of poliovirus with its counterpart from Human Rhinovirus type 2 (HRV2) eliminated the ability of the resulting chimera, PV1 (RIPO) to grow within cells of neuronal derivation. The non-pathogenic phenotype of PV1 (RIPO) and PV1 (RIPOS) was documented in mice transgenic for the human poliovirus receptor, CD155 tg mice as well as primates. See Gromeier et al., supra. Despite its inability to replicate efficiently within normal cells of neuronal origin, it is now shown that PV1 (RIPO) retained wild-type growth characteristics with an ability to lyse tumor cells in a panel of rapidly dividing malignant cell types originating from human malignancies. The types of malignancies which responded to treatment by the chimeric polioviruses included: malignant gliomas, mammary carcinoma, colorectal carcinoma, hepatocellular carcinoma, bronchial carcinoma and epidermoid carcinoma. It is suspected that the malignant cells carry the CD155 receptor to permit the entry of the recombinant chimeric polioviruses to enter and cause cytolysis of the tumor cells.

Methods of Detecting Cancer-associated Proteins

The diagnosis, classification, and characterization of tumors according to factors expressed within the tumor cell cytoplasm or on the cell surface is well established in medical oncology. Frequently, ectopic or excessive expression of molecules not ordinarily found in normal cells occurs upon malignant transformation of cells of certain organs. This principle can be used for the diagnosis, detection, differential classification, grading and staging of tumors as well as a rationale for therapeutic approaches. Detection of cell adhesion molecules belonging to the immunoglobulin superfamily has been developed as a diagnostic and classifying marker, Sasaki et al., supra. Several commonly employed assays based on immunogenic detection of specific antigens present in human tissues have been used for this purpose. For example, immunohistochemistry is being used routinely in clinical diagnostic laboratories for the classification of tumors. For this purpose, surgically excised tumor samples were embedded rapidly in a freezing compound comprising water soluble glycol and resins matrix for cryostat sectioning (Tissue Tek OCT™). Frozen sections of 5 $\mu$m thickness were made, mounted on silane coated glass slides and air dried at room temperature. The sections were fixed in acetone. The sections were treated with antibody to the specific CAM, washed and incubated with secondary anti-species antibody conjugated with horseradish peroxidase. Sections were washed thoroughly and finally incubated in a solution containing 0.6% hydrogen peroxide and the substrate diaminobenzidine tetrahydrochloride. The average staining intensity was evaluated and a comparison between the tumor sections and normal tissue sections was made. Gingras, M. -C. et al. *J. Neuroimmunol.*, (1995) 57:143–153; Tsuzuki, T. et al. *J. Clin. Pathol.*, (1998) 51:13–17. Western blot analysis has also been employed to study the presence of neural CAM in astrocytomas. Tissue in Tris-HCl buffer pH 7.4 was homogenized and centrifuged. The supernatant was subjected to SDS-polyacrylamide gel electrophoresis and transferred to polyvinylidene difluoride membranes. The blots were incubated overnight with anti-NCAM antibody ERIC-1 and visualized by an indirect secondary antibody method as described above. Blots were treated with an anti-species antibody recognizing ERIC-1 that was conjugated to horseradish peroxidase. In a staining reaction with a peroxidase substrate bands specific for NCAM could be identified. Sasaki, H. et al. *Cancer,* (1998) 82:1921–1931; Izumoto, S. et al., *Cancer Res.,* (1996) 56:1440–1444.

OBJECTIVES OF THE INVENTION

It is an objective of the present invention to develop a method to detect the presence of CD155 in human cancers.

It is another objective of the present invention to be able to use the results obtained to determine whether the use of chimeric oncolytic polioviruses would be effective for treatment of malignancy if found.

A further objective of the present invention is to develop analytical methods employing antibodies to CD155 to detect the presence of CD155 to determine the degree of malignancy and to determine whether the use of chimeric poliovirus was appropriate for the treatment of the tumor.

LIST OF REFERENCES

1. Bodian D., *Science* (1955)12:105–108.
2. Ren, R. et al., *Cell* (1990) 63:353–362.
3. Koike et al., *Proc. Natl. Acad. Sci. U.S.A.* (1991) 88:951–955.
4. Gromeier et al., *Proc. Natl. Acad. Sci. U.S.A.* (1996) 93:2370–2375.
5. Mendelsohn C. et al., *Proc. Natl. Acad. Sci.* USA (1986) 83:7845–7849.
6. Koike et al., *EMBO J.* (1990) 9: 3217–3229.
7. Wimmer et al., In: *Cellular Receptors for Animal Viruses* (1993) Cold Spring Laboratory Press: Plainview. N.Y.
8. U.S. Pat. No. 5,631,407.
9. U.S. Pat. No. 5,753,521.
10. Bernhardt et al., *Virology* (1994) 203: 344–356.
11. Chadeneau et al., *Int. J. Cancer* (1994) 68:817–821.
12. Walsh et al., *Annul Rev. Cell Dev. Biol.* (1997) 13:425–456.
13. Colamarino et al., *Annul Rev. Neurosci.* (1995) 18:497–529.
14. Nobis, P. et al. *J. Gen. Virol.,* (1985) 66:2563–2569.
15. Gromeier, M. et al., *J. Virol.,* (1999) 73:5056–60
16. Gingras, M. -C. et al. *J. Neuroimmunol.,* (1995) 57:143–153.
17. Tsuzuki, T. et al. *J. Clin. Pathol.,* (1998) 51:13–17.
18. Sasaki, H. et al. *Cancer,* (1998) 82:1921–1931.
19. Figarella-Branger et al., *Cancer Res.* (1990) 50:6364–6370.
20. Izumoto, S. et al., *Cancer Res.,* (1996) 56:1440–1444.

SUMMARY OF THE INVENTION

According to the present invention a method of determining the malignancy of tumor tissue and determining whether the use of recombinant chimeric poliovirus for treatment of the malignant tumor is appropriate has been developed. The method comprises the steps:

a) treating surgical explant tumor tissue to prepare a thin section of the tumor tissue for mounting the section on a pre-coated microscopic slide;
b) fixing and blocking the section on the slide;
c) reacting the section with an anti-CD155 monoclonal antibody to bind CD155;
d) reacting a secondary antibody conjugated to a chromophore with the bound anti-CD155 to form a complex;
e) developing a color by reacting the complex with a chromogenic substrate for the chromophore.

The tumor tissue may be prepared by either shock freezing or embedding in paraffin. Thin cryosections or paraffin-embedded sections of the tumor tissue are prepared and mounted on silane-coated microscope slides. The sections are fixed on the slides with fixing agents, such as: paraformaldehyde in phosphate buffered saline (PBS), glutaraldehyde in PBS, and acetone. The fixed tumor tissue sample is incubated from about 2 to 10 min. For detection of antibody reactivity the substrates for the chromophore may include chromogenic, fluorescent or chemiluminescent agents.

Chromogenic substrates include agents such as 5-bromo-4-chloro-3-indolyl-phosphate 4 toluidine/nitro blue tetrazolium chloride for alkaline phosphatase and 3-amino-9-ethylcarbazole for horseradish peroxidase; fluorescent substrates like 2-hydroxy-3-naphthoic acid-2'-phenylanilide phosphate/4-chloro-2-methylbenzene-diazonium hemizinc chloride for alkaline phosphatase; chemiluminescent substrates like disodium 4-chloro-3-(methoxyspiro $\{1,2\text{-}$dioxetane-3,2'-(5'-chloro) tricyclo $[3.3.1.1^{3,7}]$ decan$\}$-4-yl) phenyl phosphate for alkaline phosphate and luminol/4-iodophenol for horseradish peroxidase.

Alternatively the tumor tissue samples may be homogenized in a suitable solubilization buffer. After centrifuging and filtering to remove debris, the protein concentration of the supernatant fluid is determined and adjusted to a standard selected for all tumor samples. Then the supernatant fluid is boiled for 5 min. in a buffer, such as Laemmli buffer, and subjected to sodium-dodecyl-sulfate (SDS) polyacrylamide gel electrophoresis (PAGE). The separated proteins are Western blotted, and treated with a monoclonal anti-CD155 antibody and secondary antibody conjugated to a chromophore as described above selected to visualize the protein bands specific for CD155.

The proteins in the supernatant liquid may also be immuno-precipitated, mixed with sepharose A, equilibrated in PBS, and then mixed with ascites fluid containing a monoclonal antibody to CD155 and incubated over night. The immunoprecipitate is then boiled in Laemmli buffer and the remaining steps of the procedure as described above are followed.

The above procedures may be also modified as an immunodot assay. The tumor samples are determined at the same time as a sample that is not tumorous. By comparison, the overexpression of CD155 can be determined. According to the present invention a method for determining the expression levels of the immunoglobulin superfamily molecule CD155 has been developed. Determination of the expression levels of CD155 can be used to classify, characterize and stage malignant tumors and may provide a rationale for the use of attenuated oncolytic poliovirus as therapy.

DETAILED DESCRIPTION OF THE INVENTION

Figure 1:
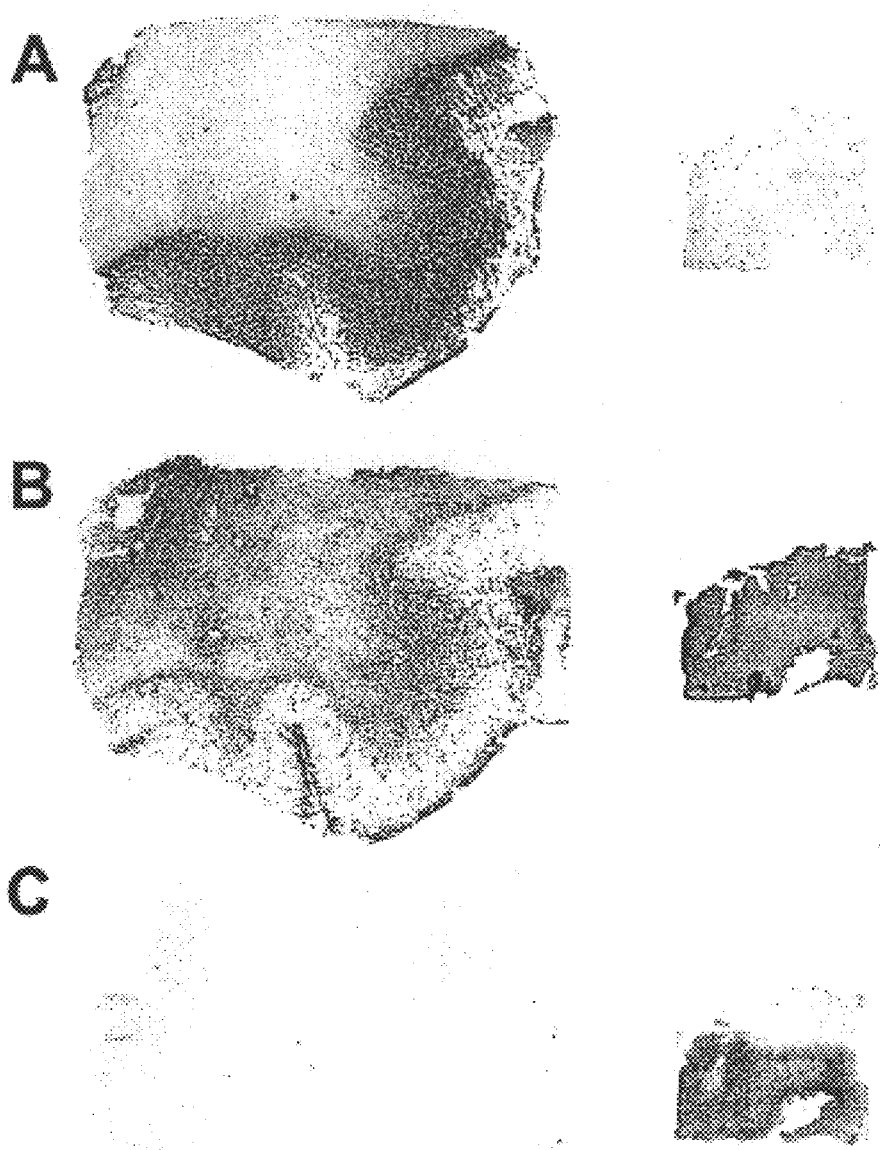
FIG. 1 shows the electronmicrographs of normal brain cells and malignant brain cells treated with A. anti-anti-NF-160 antibody; B. anti-GFAP antibody and C. CD155 antibody D171.

The method employs any of the well known immunoassay procedures wherein an antibody to CD155 is used as the primary antibody for detecting the presence of CD155, which has been found to be over expressed by cancerous cells. The antibody may be applied directly to sections of the tumor tissue. Alternatively, the antibody may be used to detect CD155 in tissue homogenates containing proteinaceous components of tumor samples separated by gel electrophoresis. The antibody may be employed to extract CD155-related antigen from tissue extracts by immunoprecipitation or immunoblot techniques. Antibodies against CD155 can be immobilized onto a matrix for the quantitative analysis of CD155 in tissue extracts by enzyme-linked immunosorbent assay (ELISA) applications. These techniques represent commonly used tests to detect antigen in tissue specimens. The procedures may be varied, combined or altered for the purpose of the planned experiment. The principle of immunogenic recognition of CD155-related material in tissue specimens may be applied to innumerable methodological variations of above mentioned approaches. These assays may be modified as long as it is the presence of CD155 in cancerous cells that is being determined. In the following, detailed protocols for the most commonly applied analytical procedures are outlined:

For direct immunohistochemical detection of CD155 on cancers the following experimental protocols may be followed:

a) treating tumor tissue immediately after surgical removal by:
  i) shock-freezing the sample immediately by one of the following steps: immersing in cold isopentane cooled on dry ice, immersing in liquid nitrogen, immersing in powdered dry ice, or submerging in a freezing compound comprising a water soluble glycol and resins matrix for cryostat sectioning (Tissue Tek OCT™) followed by placing into powdered dry ice; or
  ii) fixing the sample by using an appropriate fixing solution selected from the group consisting of: 2% neutral buffered paraformaldehyde, 2% neutral buffered paraformaldehyde/0.2% glutaraldehyde, ice cold acetone, 25% glacial acetic acid in 100% ethanol;
  iii) optionally, freezing the fixed sample by immersion in 30% sucrose in phosphate buffered saline over night and placing in a freezing compound comprising a water soluble glycol and resins matrix for cryostat sectioning (Tissue Tek OCT™) at 70° C. for at least 15 min.;
b) sectioning the samples on a cryostat into a thickness of about 5–25 $\mu$m.

Alternatively, the fixed samples may be embedded in paraffin and microtome as follows:
  i) rinse the fixed samples in PBS for approximately 30–60 min.;
  ii) transfer the samples to 70% Ethanol for at least 3 hrs. over night;
  iii) transfer the samples to 85% Ethanol for 1 hr.;
  iv) transfer the samples to 95% Ethanol for 1 hr.;
  v) transfer the samples to 100% Ethanol for 2 hrs.;
  vi) transfer the samples to a solvent selected from the group consisting of toluene and xylene for 2 hrs.;
  vii) transfer the samples to 50% toluene/50% melted paraffin for 1 hr.;
  viii) transfer the samples to 100% melted paraffin for 1–2 hrs.;
  ix) submerge the samples in melted paraffin and allow to solidify at room temperature; then cutting the paraffin fixed samples into thin 5 $\mu$m to 25 $\mu$m thick sections;
c) placing and fixing the thin sections on silane treated microscopic slides for immunohistochemical assay using anti-CD155 for determining the presence of CD155 in the tumor tissue sample.

All of the above described steps are well known and may be varied in accordance with the desired protocol. Results of the immunohistochemical procedure may vary according to the fixing protocol implemented. For example, the frozen sections may be dried at room temperature for approx. 2 min. and postfixed for 1–5 min. in an empirically determined fixing reagent, such as 2% paraformaldehyde in PBS. Alternative fixing reagents listed above may also be used. Composition of the fixing reagent and the duration of the fixing reaction may be adjusted to give optimal results. The fixed sections are then rinsed in PBS for 10 min. prior to further processing. If the sections are embedded in paraffin, they are allowed to dry on the slide over night, then subjected to the following sequence of 10 min. rinses for each solvent: 100% toluene, 100% toluene, 100% ethanol, 100% ethanol, 95% ethanol, 85% ethanol, 70% ethanol, 50% ethanol, 30% ethanol, distilled water and PBS. This ensures that the paraffin is removed and the sample is in PBS after the final rinse.

For the immunohistochemical assay, the sections are overlaid with a blocking solution containing: 3% bovine serum albumin (BSA) in PBS or other blocking reagents. The blocking reagents include non-specific serum or dry milk. The blocking treatment is allowed to proceed for 1 hr. at room temperature. Anti-CD155 antibody, e.g. D171, a murine monoclonal antibody, is diluted with PBS buffer containing 3% BSA, 0.1% TRITON X™-100, t-octylphenoxypolyethoxyethanol, at a ratio of 1:100. The sample sections are generally overlaid with the antibody solution for 16 hrs. at 4° C. The duration and temperature conditions may be varied according to the antibody selected and the material tested. The optimal conditions should be determined empirically. The antibody treated sections are then washed three times in PBS for 15 min. each to remove unbound antibody and then overlaid with PBS containing 3% BSA and a secondary antibody at a dilution of 1:2000. D171 is a murine antibody. Hence, an anti-mouse IgG antibody coupled to an enzyme for easy chromogenic detection should be used. The secondary antibodies may be coupled to a chromogenic enzyme such as: horseradish peroxidase, alkaline phosphatase, fluorescein isothiocyanate, or other suitable enzymes. Alternatively, the secondary antibody may be conjugated to biotin and used in conjunction with chromophore-labeled avidin. In the following protocol the secondary antibody coupled to horseradish peroxidase is used. Protocols that make use of other conjugates are conceptually similar. Minor adjustments may be necessary to allow for the specific conditions of the substrate conversion reaction.

The following is a standard protocol for developing the chromogenic response in an immunohistochemical assay. The antibody treated Sections are washed three times in PBS for 15 min. each to remove unbound antibody.
  i) immersing the CD155 antibody treated sections for 5 min. in acetate buffer comprising: 0.01 M acetic acid, 0.035M sodium acetate trihydrate, at pH 5.4,
  ii) developing the color by immersing the sections in an acetate buffer containing a substrate for horseradish peroxidase and 0.6% hydrogen peroxide.
  iii) rinsing the sections in PBS and distilled water and drying and mounting the rinsed sections with an appropriate mounting medium.

The variety of chromophores reactive to a wide selection of chromogenic, fluorogenic or chemiluminescent substrates suitable for the immunohistochemical detection of CD155 are described above.

Recently developed immunohistochemical protocols with increased sensitivity may also be employed. The procedure may employ peroxidase-anti-peroxidase (PAP) complex or the avidin-biotin (ABC) complex, or labelled streptavidin for developing the chromogenic response. The protocol for the PAP process includes the following steps:
a) obtaining, treating and sectioning a tumor tissue sample as described above for steps (a) to (c);
b) immersing the sections with a solution of a bridging rabbit anti-mouse antibody in PBS containing 3% BSA for about 1 hr. at room temperature;

c) washing the immersed sections in PBS three times for about 15 min. each;
d) immersing the sections in PAP in PBS for about 30 min. at room temperature;
e) washing the sections in PBS three times;
f) developing the sections as described above in steps (i)–(iii).

In place of the PAP, the avidin-biotin complex or labelled avidin may be employed. The avidin may be replaced by streptavidin/horse radish peroxidase complex. The color development is as described above in steps (d)–(f). The blocking agents, conditions of antibody incubation, reporter emzyme, detection system, the enzyme substrate may be varied as desired in accordance with known protocols.

Western blotting may also be used for detection of CD155 in cancers. The following experimental protocols are exemplary:

g) obtaining surgical explant tumor tissue and either use it immediately for the following assay or shock-freeze the material for storage and future analysis;
h) placing 50–500 mg of tumor tissue in 200 µl of a solubilization buffer (PBS containing 5% NP40, non-ylphenoxy polyethoxy ethanol) and homogenizing the mixture for 10 min. on ice to completely disintegrate the tumor tissue;
i) centrifuging the homogenized and disintegrated material to remove undissolved debris, and separate the supernatant;
j) determining the protein concentration of the supernatant fluid and adjusting the concentration to a standard to be determined for all tumor samples to be tested;
k) preparing the homogenized sample for gel electrophoresis by boiling for 5 min. in Laemmli buffer comprising 2% sodium dodecyl sulfate (SDS), 5% β-mercaptoethanol, 10% glycerol, and 50 mM Tris HCl, at pH 6.8;
l) subjecting the material to SDS polyacrylamide gel electrophoresis (PAGE);
m) blotting the separated proteins within the gel onto a nitrocellulose filter in a Western blot apparatus over night;
n) removing the nitrocellulose filter and blocking with TBST, comprising 10 mM Tris at pH 8.0 in 0.05% TWEEN™-20, polyoxyethylenesorbitan, containing 3% fat free dry milk powder for 60 min. at room temperature;
o) incubating the filter for specific detection of CD155 proteins for 3–6 hrs. at room temperature with monoclonal anti-CD155 antibody elicited from an animal species in TBST, 10 mM Tris buffer at ph 8.0 in 0.05% TWEEN™-20, polyoxyethylenesorbitan, containing 3% fat free milk powder at a dilution of 1:1000;
p) washing the filter for three times 15 min. each with fresh changes of TBST;
q) treating the filter with a secondary anti-species antibody-conjugate diluted in TBST 1:2000. Various chromophores coupled to the secondary anti-species antibody may be selected for the purpose of detection of immunoreactivity (see above);
r) washing the filter for three times 15 min. each with fresh changes of TBST;
s) rinsing the filter for 5 min. in acetate buffer;
t) developing the filter with a chromogenic or chemiluminescent substrate of horseradish peroxidase to visualize the bands corresponding to the protein CD155 on the filter.

The same chromogenic substrates as used in immunohistochemical applications may be employed as described above. A chemiluminescence detection kit (Boehringer Mannheim) may also be employed. In this case, the filter is exposed to a chemiluniscent substrate and subsequently overlaid with x-ray film capable of capturing the chemiluminescent energy. The exposed x-ray film is developed to visualize areas of immunoreactivity on the filter.

Anti-CD155 antibodies other than D171 may be useful for this technique. The specific conditions such as the incubation duration and temperature may be varied in accordance with the antibody species.

Alternatively, the experimental protocols for a combined Immunoprecipitation/Western blotting technique may be followed:

a) Obtaining, freezing or fixing and homogenizing the tumor tissue as described above for steps (a) to (d);
b) immunoprecipitating the tumor sample by mixing 25 mg of protein A/sepharose, equilibrated in PBS, with 250 µl of ascites fluid containing a monoclonal antibody to CD155 and incubate over night;
c) boiling a fraction of the immunoprecipitated material for 5 min. in Laemmli buffer to prepare for SDS-PAGE;
d) following the procedure as described in (f)—(n) above for the Western blot procedure for the chromogenic or chemiluniscent detection of immunoprecipitated CD155 in tumor homogenates.

Alternatively, as a precipitating matrix, protein G or other materials with affinity for antibodies maybe employed;

The detection of CD155 in cancers may also be conducted by immunoblotting using the following experimental protocols:

a) obtaining and treating tumor tissue samples as described in steps (a) to (d);
b) blotting a standard amount of tumor homogenate onto a suitable carrier membrane, e.g., a nitrocellulose membrane;
c) drying the blotted membrane at room temperature
d) proceeding as in h.—n. above for the Western blotting procedure for the visualization of CD155 specific material in tumor homogenate directly blotted onto carrier membranes.

The specific steps, conditions to be used may be varied as long as an antibody to CD155 is used to detect the over expression of CD155 by tumor cells. The over expression of CD155 can serve as an indication of malignancy and the stage of malignancy. The result may also be used to determine whether treatment with chimeric poliovirus would be effective to cause cytolysis of the cancerous cells. In the experiments conducted D171 was used as the antibody to CD155. However, other antibodies to CD155 may be employed. These may be obtained by following the procedure described by Nobis et al, supra. The following examples are provided for purposes of illustration and are not to be construed as limiting the scope of the invention.

EXAMPLE 1

Immunohistochemistry of Normal Brain Tissue and Malignant Gliomas

Resected tumor and normal brain tissue were obtained during craniotomy from patients diagnosed with tumorous growths within their central nervous system. The tissue specimens were treated in accordance with one of the following procedures:

immediately placed in a fixing compound such as OCT (Fisher Co.) and gently frozen on dried ice, immediately submerged in isopentane which was cooled in liquid nitrogen, or fixed for 3 hours in 2% neutral buffered formaldehyde at 4° C., then submerged in 30% sucrose in phosphate buffered saline overnight at 4° C., and embedded in OCT and frozen on dry ice.

The frozen tissue samples were cryo-sectioned at a thickness of 10–16 μm and placed on microscope slides previously treated with Aminoalkylsilane. See, Rentrop, M. et al. *Histochem. J.*, (1986) 18:271–276. The sections were air dried for 3–5 min. and then fixed in 2% neutral buffered paraformaldehyde for 10 min. at room temperature. The fixed sections were transferred to PBS for storage for up to a maximum of a week.

The stored sections were then washed twice with cold PBS and immersed in PBS containing 3% bovine serum albumin and 0.1% sodium azide for 60 min. at room temperature. The sections were then treated with a first monoclonal anti-CD155 antibody D171 1:100 in PBS containing 3% bovine serum albumin and 0.1% sodium azide over night at 4° C. The solution was removed and the slides were thoroughly washed with PBS in three individual steps of 15 min each to remove unbound antibodies. After the last washing cycle, the sections were treated with a second antibody, which is an anti-mouse antibody, labeled with horse radish peroxidase at 1:100 in PBS containing 3% bovine serum albumin for 60 min. at room temperature.

Subsequently, the second antibody was removed with PBS in three individual washing steps of 15 min each. The washed sections were submerged in an acetate buffer containing 0.015M acetic acid, 0.035M sodium acetate trihydrate. The slides were then placed into a staining solution containing tablet of 3-amino-9-ethylcarbazole (Sigma Co.) in 2.5 mL dimethyl formamide diluted with 47.5 mL of the acetate buffer and stirred with 30 μL hydrogen peroxide immediately prior to use. After 2–3 min the slides were washed with PBS and then distilled water, dried and covered with CRYSTAL MOUNT® mounting medium (Fisher Co.)

Following the same procedure described above, normal brain tissue and brain tumor tissue were treated except that the first antibody was replaced with anti-NF160 antibody, and anti-GFAP antibody, and for comparison purposes left untreated. The results shown in FIG. 1 demonstrate that the procedure was excellent for determining expression of CD155 in human tissues, malignant or not. As can be seen in FIG. 1, using a monoclonal antibody to 160 kD neurofilament (NF-160; FIG. 1A, left), the method described yields intense immunoreactivity within the cerebral cortex. This is to be expected, since the cortex is mainly composed out of neuronal cells expressing neurofilaments. Using a monoclonal antibody against GFAP (glial fibrillary acidic protein, an astrocytic marker) mainly white matter of the cortex is stained positively (FIG. 1B, left). Again, this is expected, since the white matter contains cells that produce GFAP. Gliomas typically do not express neurofilaments because they are not of neuronal lineage (hence FIG. 1A, right, shows negative staining with anti-NF160 in glioma tissue). However, they commonly do express GFAP because of their glial ancestry (not surprisingly, the glioma section shown reacted strongly with anti-GFAP antibody; FIG. 1B, right). CD155 apparently is expressed within normal human brain at levels below the detection threshold for the immunohistochemical assay described. Therefore, FIG. 1C (left) does not show positive signal within the cerebral cortex using an anti-CD155 antibody (D171). However, as evident from FIG. 1C (right), gliomas do express CD155 in sizable quantities. The results demonstrated that the procedure was excellent for the detection of the presence of CD155 on glioma tissue and the absence of CD155 on normal brain tissue.

EXAMPLE 2

Immunohistochemistry of CD155 in Malignant Gliomas

Twenty seven specimens were collected from patients diagnosed with various malignant gliomas and assayed in accordance with the procedure described in Example 1 using as the first antibody, anti-GFAP or anti-CD155 for side by side comparison. Anti-GFAP antibody was used as the primary antibody in each control sample to show that the procedure was working properly. The results are presented in Table 1.

Based on the results obtained using antibodies to CD155 in the immunohistochemical procedure according to the present invention and the diagnosis obtained from pathological studies, the present method is appropriate not only for determining the presence of CD155 receptor on tissue and is also useful for determining the stage of tumor development and whether treatment with chimeric poliovirus was appropriate.

In Table 1, +++ corresponds to very strong-, ++ to strong-, + to moderate, and +/− to weak expression levels of CD 155. We observed a general trend for lower malignant gliomas (e.g. tumor #SB8209, 95, 53, 71, 122, 51, 84, 78, 18) to express CD155 at higher levels than the highly malignant glioblastomas multiforme (e.g. tumor #37, 22, 16). This quantitative difference in CD155 expression may reflect differences in malignancy, invasive behavior or other properties that may be of diagnostic or prognostic value.

TABLE 1

| Specimen | Tumor Type | GFAP | CD155 |
|---|---|---|---|
| SB8209 | ganglioglioma | +++ | +++ |
| 95 | oligodendroglioma | +++ | +++ |
| 53 | glioma | +++ | +++ |
| 71 | oligodendroglioma | +++ | ++ |
| 122 | astrocytoma | +++ | ++ |
| 51 | oligodendroglioma | +++ | ++ |
| 84 | anaplastic astrocytoma | +++ | +++ |
| 78 | anaplastic astrocytoma | +++ | +++ |
| 18 | anaplastic astrocytoma | +++ | ++ |
| 35 | anaplastic astrocytoma | +++ | ++ |
| 56 | anaplastic oligodendroglioma | +++ | ++ |
| 31 | anaplastic oligodendroglioma | +++ | − |
| 15 | high grade astrocytoma | +++ | + |
| 82 | glioblastoma multiforme | +++ | + |
| 29 | glioblastoma multiforme | +++ | + |
| 34 | glioblastoma multiforme | +++ | + |
| 36 | glioblastoma multiforme | +++ | + |
| 41 | glioblastoma multiforme | +++ | + |
| 4 | glioblastoma multiforme | +++ | +/− |
| 17 | glioblastoma multiforme | +++ | +/− |
| 21 | glioblastoma multiforme | +++ | +/− |
| 26 | glioblastoma multiforme | +++ | +/− |
| 16 | glioblastoma multiforme | +++ | − |
| 22 | glioblastoma multiforme | +++ | − |
| 37 | glioblastoma multiforme | +++ | − |
| 38 | malignant meningioma | | ++ |
| 39 | malignant meningioma | | ++ |

EXAMPLE 3

Immunohistochemical Detection of CD155 in Other Tumors

Sample of malignant tumors of the lung, breast, colon, bladder and salivary glands were obtained and tested in accordance with the procedure described in Example 1 using as the primary antibody, D171.

The results are presented in Table 2. The specific type of cancer for each of the tumor tissue is indicated.

TABLE 2

| Specimen | Tumor Type | CD155 |
|---|---|---|
| 2451 | bronchiocarcinoma squamous cell ca | +++ |
| 2345 | bronchiocarcinoma squamous cell ca | +++ |
| 2527 | bronchiocarcinoma adeno ca | +++ |
| 2593 | bronchiocarcinoma squamous cell ca | +++ |
| 2617 | bronchiocarcinoma squamous cell ca | +++ |
| 2625 | bronchiocarcinoma squamous cell ca | +++ |
| 3106 | bronchiocarcinoma adeno ca | +++ |
| 3108 | bronchiocarcinoma adeno ca | +++ |
| 2732 | bronchiocarcinoma adeno ca | ++ |
| 3362 | Mammary carcinoma invasive ductal ca | +++ |
| 3429 | Mammary carcinoma in situ/invasive ductal ca | +/− |
| 3433 | Mammary carcinoma in situ/invasive ductal ca | + |
| 6901 | Mammary carcinoma in situ/invasive ductal ca | ++ |
| 6708 | Mammary carcinoma invasive ductal ca | ++ |
| 6097 | Mammary carcinoma in situ/invasive ductal ca | +++ |
| 5857 | Mammary carcinoma in situ/invasive ductal ca | + |
| 5124 | Mammary carcinoma in situ/invasive ductal ca | − |
| 675 | colon carcinoma adeno ca | +++ |
| 608 | colon carcinoma adeno ca | +++ |
| 657 | colon carcinoma adeno ca | +++ |
| 5546 | colon carcinoma adeno ca | +++ |
| 5478 | colon carcinoma adeno ca | +++ |
| 5546 | colon carcinoma adeno ca | +++ |
| 5478 | coion carcinoma adeno ca | ++ |
| 5426 | colon carcinoma adeno ca | +++ |
| 5424 | colon carcinoma adeno ca | ++ |
| 5267 | colon carcinoma adeno ca | +++ |
| 4991 | colon carcinoma adeno ca | +++ |
| 4734 | colon carcinoma adeno ca | +++ |
| 5334 | colon carcinoma adeno ca | ++ |
| 4538 | bladder carcinoma | +++ |
| 4788 | bladder carcinoma | +++ |
| 4722 | bladder carcinoma | +++ |
| 2249 | parotis carcinoma | − |
| 755 | parotis carcinoma | +/0 |

EXAMPLE 4

Detection of CD155 in Tumor Tissue Homogenates by a Combined Immunoprecipitation/Western Blot Protocol Brain tumor tissue and normal brain tissue was obtained from patients undergoing craniotomy for the removal of a malignant glioma. The tissue was immediately frozen in dry ice and stored a −70° C. Tissue fragments were placed at room temperature, immersed in dissociation buffer (PBS containing 0.5% NP40, nonylphenoxy polyethoxy ethanol) and subsequently homogenized in a Dounce homogenizer.

The homogenate was centrifuged and the supernatant was removed.

Prior to this assay, protein A/sepharose that had been equilibrated in PBS was incubated over night with the mouse monoclonal anti-CD155 antibody D171. After three washes of the protein A/sepharose complex, 25 μl of the mix was added to the homogenized tumor tissue supernatant. The solution containing the protein A/sepharose-D171 complex was incubated at 4° C. over night. The sepharose beads were gently centrifuged and washed three times to remove unbound tumor material. The resulting pellet was then prepared for SDS-PAGE by adding Laemmli buffer prior to boiling for 5 min. The samples were loaded on a 12.5 polyacrylamide gel. After the samples had been run on the polyacrylamide gel, the gel was placed onto a nitrocellulose membrane and put into a Western blot apparatus for transfer of the protein bands separated with gel electrophoresis onto the nitrocellulose membrane. The transfer was allowed to proceed over night at 4° C.

Figure 2:
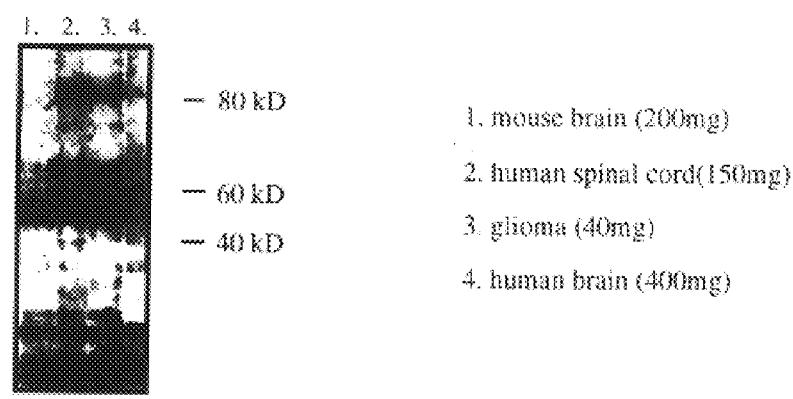
FIG. 2 shows the results of chemiluminescent detection of CD155 using anti-CD155 antibody D171 by a combined immunoprecipitation/Western blot approach.

Afterwards, the nitrocellulose filter was removed and immediately placed in TBST, 10 mM Tris buffer, pH 8.0 in 0.05% TWEEN™-20, polyoxyethylenesorbitan, containing 3% fat free dry milk powder. The membrane was gently agitated in the blocking buffer for 1 hr. at room temperature. Subsequently, the monoclonal anti-CD155 antibodies D171 and P44 were diluted 1:1000 in TBST and the resulting solution was used to treat the membranes for 3 hrs. at room temperature. Following incubation with the primary antibodies, the membrane was washed with TBST in three consecutive steps. The secondary antibody (horseradish peroxidase conjugated anti-mouse IgG) was diluted 1:2000 in TBST. The membrane was immersed into this solution and incubated for 1 hr. at room temperature. Following treatment with the secondary antibody, the membrane was washed with TBST for three consecutive cycles. Thereupon, the membrane was placed into acetate buffer (0.015M acetic acid, 0.035M sodium acetate trihydrate) for 5 min. at room temperature. Finally the membrane was treated with a chemiluminescent substrate provided by a chemiluminescence detection kit (Boehringer Mannheim) and exposed to x-ray film to reveal the presence of immunoreactivity of monoclonal anti-CD155 antibodies D171 and P44. FIG. 2 shows the results of chemiluminescent detection of CD155 by a combined immunoprecipitation/Western blot approach, on the blot several bands corresponding to the antibodies used in the immunoprecipitation and CD155-specific polypeptides can be distinguished. Bands around 60 kD correspond to the heavy chain fractions of antibodies D171 and P44 employed in the immunoprecipitation reaction. Bands around 25 kD correspond to the light chains of these antibodies. Bands at about 80 kD correspond to CD155 immunoprecipitated from organ homogenate supernatants. See the above description of experimental protocols. Lane 1 contains organ homogenate from mouse brain run on a SDS-PAGE gel. Since mice do not express CD155, no immunoprecipitable material was recognized in the blot. Norman human spinal cord (lane 2), as expected to express CD155 because it harbors anterior horn motor neurons susceptible to poliovirus, and is recognized by the anti-CD155 antibody D171. Lane 3, derived from a human astrocytoma (a surgically excised tissue sample homogenate), contained a vast excess of CD155. In contrast CD155 was hardly detectable in homogenates derived from human brain (lane 4). The CD155-specific band from the tumor homogenate was substantially stronger that the corresponding band from human normal brain, despite the fact that only one-tenth of tumor tissue (compared to brain tissue) had been used to produce the homogenate. This observation demonstrates the excessive levels of CD155 expression detectable by a combined immunoprecipitation/Western blot approach described in this application.

What is claimed is:

1. A method for detecting CD155 in tumor tissue comprising the steps:
   a) treating a surgical explant tumor tissue to prepare a thin section of the tumor tissue for mounting the section on a pre-coated microscopic slide;
   b) fixing and blocking the section on the slide;
   c) reacting the section with an anti-CD155 monoclonal antibody to bind CD155;
   d) reacting a secondary antibody conjugated to a chromophore with the bound anti-CD155 to form a complex;
   e) developing a color by reacting the complex with a chromogenic substrate for the chromophore; and
   f) detecting the presence of color which indicates the presence of CD155.

2. The method according to claim 1 wherein the monoclonal antibody which binds to CD155 is D171.

3. The method according to claim 1, wherein step a) is selected from a group consisting of:
   i) obtaining and immediately placing tumor tissue in a fixing compound and gently freezing the tumor tissue on dried ice,
   ii) obtaining and shock freezing tumor tissue by immersing rapidly in cooled isopentane; liquid nitrogen; powdered dry ice; or a freezing compound comprising a water soluble glycol and resins matrix for cryostat sectioning followed by placing in powdered dry ice;
   iii) fixing tumor tissue in a fixing solution selected from the group consisting of 2% neutral buffered paraformaldehyde, 2% neutral buffered paraformaldehyde/0.2% glutaraldehyde, ice cold acetone, and 25% glacial acetic acid in 100% alcohol.

4. The method according to claim 3 wherein the fixing compound in step a) is a freezing compound comprising a water soluble glycol and resins matrix for cryostat sectioning and gently freezing the tumor tissue on dried ice.

5. The method according to claim 3 wherein step a) is: obtaining and fixing tumor tissue for 3 hours in 2% neutral buffered paraformaldehyde at 4° C., submerging the tumor tissue in 30% sucrose in phosphate buffered saline overnight at 4° C., and then submerging in a freezing compound comprising a water soluble glycol and resins matrix for cryostat sectioning and freezing on dry ice.

6. The method according to claim 3 wherein step a) is: embedding the fixed tumor tissue in paraffin microtome into thin sections for placing on microscopic slides.

7. A method for detecting CD155 in tumor tissue by an immunoassay comprising the steps:
   a) homogenizing 50–500 mg of surgical explant tumor tissue in about 200 μl of a solubilization buffer comprising PBS containing 0.5% nonylphenoxy polyethoxy ethanol (SP40™) for 10 min. on ice to completely disintegrate the tumor tissue;
   b) centrifuging the homogenized tumor tissue to separate out the supernatant fluid;
   c) detecting the presence of CD155 in the supernatant fluid in an immunodot assay, an immunoprecipitation assay, an immunoblot assay or an ELISA procedure wherein the binding of a monoclonal anti-CD155 antibody to the tumor tissue indicates the presence of CD155 in the tumor tissue.

8. The method according to claim 7 wherein the immunoassay is an immunodot assay and comprises the following steps:
   a) determining the protein concentration of the supernatant fluid and adjusting the protein concentration to a standard selected for all tumor samples to be tested;
   b) preparing the homogenized sample for gel electrophoresis by boiling for 5 min. in Laemmli buffer comprising 2% sodium dodecyl sulfate (SDS), 5% β-mercaptoethanol, 10% glycerol, and 50 mM Tris HCl, at pH 6.8;
   c) subjecting the material to SDS polyacrylamide gel electrophoresis (PAGE);
   d) blotting the separated proteins within the gel onto a nitrocellullose filter in a Western blot apparatus over night;
   e) removing the nitrocellulose filter and blocking with TBST, comprising 10 mM Tris at pH 8.0 in 0.05% polyoxyethylenesorbitan (TWEEN-20), containing 3% fat free dry milk powder for 60 min. at room temperature;
   f) incubating the filter in TBST for specific detection of CD155 proteins for 3–6 hrs. at room temperature with monoclonal anti-CD155 antibody elicited from an animal species;
   g) washing the filter to remove unbound anti-CD155 antibody;
   h) treating the filter with a secondary anti-species antibody-chromophore conjugate diluted in TBST;
   i) washing the filter to remove any unbound secondary anti-species antibody-chromophore conjugate;
   j) developing the filter with a substrate of the chromophore selected from the group consisting of chromogenic and chemiluminescent substrates to visualize the bands corresponding to the protein CD155 on the filter.

9. The method according to claim 8 wherein for step j) the substrate is chromogenic.

10. The method according to claim 7 wherein the immunoassay is an ELISA procedure comprising the following steps:
   a) coating a solid phase with the supernatant fluid for about 1 hour at 37° C.;
   b) incubating the coated solid phase with gelatin in PBS at 37° C. for an hour to block non-specific protein binding sites, washing and drying the coated solid phase substrate;
   c) contacting the coated solid phase substrate with an anti-CD155 antibody for about 30 min. at 37° C. to allow binding of the anti-CD155 antibody;
   d) washing the solid phase substrate to remove unbound antibodies;
   e) contacting the bound antibodies with a secondary antibody conjugated to horse radish peroxidase to bind to the bound anti-CD155 antibodies;
   f) washing the coated solid phase and adding orthophenylenediamine and hydrogen peroxide in citrate buffer as a chromogenic substrate to react with the horseradish peroxidase to form a color product;
   g) stopping the reaction with 1M $H_2SO_4$ and measuring the color at $A_{492}$ nm.

11. The method according to claim 7, 8, 9 or 10 wherein the anti-CD155 antibody is D171.

12. A method for detecting CD155 in tumor tissue comprising the steps:
   a) treating tumor tissue immediately after surgical removal by one of the following steps:
      i) shock-freezing the tumor tissue immediately by one of the following steps: immersing in cold isopentane cooled on dry ice, immersing in liquid nitrogen, immersing in powdered dry ice, or submerging in a freezing compound comprising a water soluble glycol and resins matrix for cryostat sectioning, followed by placing into powdered dry ice; or
      ii) fixing the sample by using an appropriate fixing solution selected from the group consisting of: 2% neutral buffered paraformaldehyde, 2% neutral buffered paraformaldehyde/0.2% glutaraldehyde, ice cold acetone, 25% glacial acetic acid in 100% ethanol; or
      iii) freezing the fixed sample by immersion in 30% sucrose in phosphate buffered saline over night and placing in a freezing compound comprising a water soluble glycol and resins matrix for cryostat sectioning at −70° C. for at least 15 min.;

b) sectioning the tumor tissue on a cryostat into a thickness of about 5–25 μm;

c) placing and fixing the thin sections on silane treated microscopic slides for immunohistochemical assay using as a primary antibody a monoclonal anti-CD155 antibody for detecting the presence of CD155 in the tumor tissue;

d) developing and detecting a chromogenic response by:
   i) immersing the sections for 5 min. in acetate buffer comprising: 0.01M acetic acid, 0.035M sodium acetate trihydrate, at pH 5.4,
   ii) developing the color by immersing the sections in an acetate buffer containing a substrate for horseradish peroxidase and 0.6% hydrogen peroxide,
   iii) rinsing the sections in PBS and distilled water and drying and mounting the rinsed sections with an appropriate mounting medium, and e) detecting the presence of color in the tumor tissue which indicates the presence of CD155.

13. The method according to claim 12 wherein the primary anti-D155 antibody is D171.

* * * * *